United States Patent

Kudo et al.

[11] Patent Number: 4,786,719
[45] Date of Patent: Nov. 22, 1988

[54] DNA SEQUENCE

[75] Inventors: Akira Kudo; Yushi Nishimura, both of Fukuoka; Yataro Ichikawa, Tokorozawa; Takeshi Watanabe, Saga, all of Japan

[73] Assignee: Teijin, Limited, Osaka, Japan

[21] Appl. No.: 790,970

[22] Filed: Oct. 24, 1985

[30] Foreign Application Priority Data

Oct. 26, 1984 [JP] Japan .................. 59-224205

[51] Int. Cl.⁴ .................. C07H 19/10; C07H 19/20; C07H 21/02; C07H 21/04
[52] U.S. Cl. .................. 530/388; 414/85.8; 514/8; 530/387; 530/389; 530/390; 530/391; 536/27; 536/28; 536/29; 935/15
[58] Field of Search .................. 536/27, 28, 29; 530/387, 388

[56] References Cited

PUBLICATIONS

Kudo et al, (I), J. Immunology, vol. 135, pp. 642-645, 1985 (Jul.).
Brodeur et al., European J. Immunology, vol. 14, pp. 922-930, 1984.
Xancopolous et al., Nature, vol. 311, pp. 727-733, 1984.
Kudo et al, (II), Gene, vol. 33, pp. 181-189, 1985 (Apr. '85).

Primary Examiner—J. R. Brown
Assistant Examiner—L. Eric Crane
Attorney, Agent, or Firm—Wenderoth, Lind & Ponack

[57] ABSTRACT

A DNA sequence comprising a polynucleotide segment consisting of a DNA sequence (A) shown below and a DNA sequence complementary thereto:

GATGTGCAGCTGGTGGAGTCTGGGGGAGGCTTA
　　　　　　　　　　　　　　　　　　GTGCAGCCT
GGAGGGTCCCGGAAACTCTCCTGTGCAGCCTCT
　　　　　　　　　　　　　　　　　　GGATTCACT
TTCAGTAGCTTTGGAATGCACTGGGTTCGTCAG
　　　　　　　　　　　　　　　　　　GCTCCAGAG
AAGGGGCTGGAGTGGGTCGCATATATTAGTGGT
　　　　　　　　　　　　　　　　　　GGCAGTTAT
ACCATCTACTATGCAGACACAGTGAAGGGCCGA
　　　　　　　　　　　　　　　　　　TTCACCATC
TCCAGAGACAATCCCAAGAACACCCTGTTCCTA
　　　　　　　　　　　　　　　　　　CAAATGACC
AGTCTAAGGTCTGAGGACACGGCCATGTATTAC
　　　　　　　　　　　　　　　　　　TGTGCAAGT
TCCTATGGTAACTTCTGGTACTTCGATGTCTGG
　　　　　　　　　　　　　　　　　　GGCGCAGGG
ACCACGGTCACCGTCTCCTCA wherein A represents deoxyadenosine-5'-phosphate, C represents deoxycytidine-5'-phosphate, G represents deoxyguanosine-5'-phosphate, and T represents deoxythymidine-5'-phosphate.

The DNA sequence provided by this invention is derived from a rearranged immunoglobulin heavy chain variable ($V_H$) region gene taken from the mouse hybridoma NL-1 cells which produce an antibody capable of commonly recognizing surface antigens of various human acute lyphocytic leukemia cells. Accordingly, if, for example, it is combined with a heavy chain constant ($C_H$) region gene, a heavy chain can be produced which can recognize commonly various human acute lymphocytic leukemia cells in combination with a proper light chain. This would serve for the diagnosis and treatment of human acute lymphocytic leukemia.

4 Claims, 1 Drawing Sheet

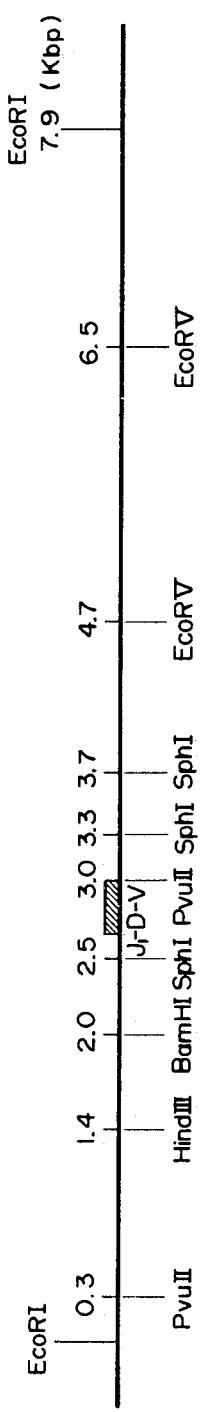

DNA SEQUENCE

This invention relates to a novel DNA sequence, and more specifically to a DNA sequence derived from a rearranged immunoglobulin heavy chain variable ($V_H$) region gene taken from the cells of a mouse hybridoma, NL-1, which produces an antibody to the common human acute lymphocytic leukemia antigen.

It has already been reported that the mouse hybridoma NL-1 produces an antibody to the common human acute lymphocytic leukemia antigen [see R. Ueda et al., Proc. Natl. Acad. Sci., USA, vol. 79, pp. 4386-4390, July 1982, Immunology]. This paper only discloses the serological analysis of cell surface antigens of null cell acute lymphocytic leukemia by mouse monoclonal antibodies that are produced by the mouse hybridoma NL-1, and fails to elucidate such antibodies from a viewpoint of molecular genetics.

Generally, immunoglobulins are composed of heavy chains (H chains) and light chains (L chains). Each of an H-chain and an L-chain has a V region having the function of specifically binding to an antigen and a C region having an effector function.

It is known that immunoglobulins produced by the mouse hybridoma, NL-1, act commonly on various types of human acute lymphocytic leukemia. But the structure of a V-region gene defining specificity for binding to an antigen has not yet been elucidated.

The present inventors have made investigations in order to elucidate the structure of the V region ($V_H$) gene in the immunoglobin H-chains in the hybridoma NL-1, and have now succeeded in cloning a DNA fragment containing the V region ($V_H$) and determining its DNA sequence.

According to this invention, there is provided a DNA sequence comprising a polynucleotide segment consisting of a DNA sequence (A) shown below and a DNA sequence complementary thereto.

DNA sequence (A):

GATGTGCAGCTGGTGGAGTCTGGGGGAGGCTTA
GTGCAGCCT
GGAGGGTCCCGGAAACTCTCCTGTGCAGCCTCT
GGATTCACT
TTCAGTAGCTTTGGAATGCACTGGGTTCGTCAG
GCTCCAGAG
AAGGGGCTGGAGTGGGTCGCATATATTAGTGGT
GGCAGTTAT
ACCATCTACTATGCAGACACAGTGAAGGGCCGA
TTCACCATC
TCCAGAGACAATCCCAAGAACACCCTGTTCCTA
CAAATGACC
AGTCTAAGGTCTGAGGACACGGCCATGTATTAC
TGTGCAAGT
TCCTATGGTAACTTCTGGTACTTCGATGTCTGG
GGCGCAGGG
ACCACGGTCACCGTCTCCTCA

In the above sequence (A), A represents deoxyadenosine-5'-phosphate; C, deoxycytidine-5'-phosphate; G, deoxyguanosine-5'-phosphate; and T, deoxythymidine-5'-phosphate.

The DNA sequence of this invention comprising the above polynucleotide segment may also be translated as encoding a polypeptide having the following amino acid sequence.

Asp Val Gln Leu Val Glu Ser Gly Gly Gly Leu Val
Gln Pro Gly Gly Ser Arg Lys Leu Ser Cys Ala Ala
Ser Gly Phe Thr Phe Ser Ser Phe Gly Met His Trp

-continued
Val Arg Gln Ala Pro Glu Lys Gly Leu Glu Trp Val
Ala Tyr Ile Ser Gly Gly Ser Tyr Thr Ile Tyr Tyr
Ala Asp Thr Val Lys Gly Arg Phe Thr Ile Ser Arg
Asp Asn Pro Lys Asn Thr Leu Phe Leu Gln Met Thr
Ser Leu Arg Ser Glu Asp Thr Ala Met Tyr Tyr Cys
Ala Ser Ser Tyr Gly Asn Phe Trp Tyr Phe Asp Val
Trp Gly Ala Gly Thr Thr Val Thr Val Ser Ser In the above amino acid sequence, the various abbreviations stand for the following amino acids.

Gly: glycine
Ala: alanine
Val: valine
Leu: leucine
Ile: isoleucine
Ser: serine
Asp: aspartic acid
Lys: lysine
Arg: arginine
His: histidine
Phe: phenylalanine
Tyr: tyrosine
Thr: threonine
Cys: cysteine
Met: methionine
Glu: glutamic acid
Trp: tryptophan
Pro: proline
Asn: asparagine
Gln: glutamine It should be understood therefore that the DNA sequence provided by this invention is not limited to one consisting only of the sequence (A) given above, but may comprise another DNA sequence so long as the DNA sequence of the invention codes for the amino acid sequence indicated above.

Investigations of the present inventors have shown that by joining the 3'-terminus of a polynucleotide consisting of a DNA sequence (B) shown below and a DNA sequence complementary thereto to the upstream side of the 5'-terminus of the above polynucleotide consisting of the DNA sequence (A) and the DNA sequence complementary thereto, the DNA sequence (B) functions as a promoter and consequently, the DNA sequence of the invention comprising the above two sequences (A) and (B) has a possibility of expressing the function of producing a polypeptide having the above amino acid sequence.

DNA sequence (B):

GCATGCTATAGAGGAAGATATGCAAATAATTCTTCTC
TGAGTTCATATAAACCAGCCCTGCCCCGAGTCTGTA
GCTCTGACAGAGGAGCCAAGCCCTGGATTCCCAGGT
CCTCACATTCAGTGATCAGCACTGAACACAGACCAC
TCACCATGGACTCCAGGCTCAATTTAGTTTTCCTTG
TCCTTATTTTAAAAGGTAATTTGTAGAGATGAGTTTC
TGCCTGTTGTGTGCCCAAGGGAAATAGAAACATTG
TTTGTTTCATTATTTTATTTTGTTAGTAACAGTTTTC
TGACCAGCATTCTCTGTTTGCAGGTGTCCAGTGT

In the DNA sequence (B), A, T, G and C are as defined above.

The DNA sequence provided by this invention is derived from a rearranged immunoglobulin heavy chain variable ($V_H$) region gene taken from the mouse hybridoma NL-1 cells which produce an antibody capable of commonly recognizing surface antigens of various human acute lyphocytic leukemia cells. Accordingly, if, for example, it is combined with a heavy chain constant ($C_H$) region gene, a heavy chain can be produced which can recognize commonly various human acute lymphocytic leukemia cells in combination with a proper light chain. This would serve for the diagnosis and treatment of human acute lymphocytic leukemia.

The FIGURE shows the restriction map for the disclosed rearranged immunoglobulin heavy chain variable region gene taken from mouse hybridoma NL-1 cells, with the $V_H$ gene location noted.

The following Examples illustrate the present invention without any intention of limiting the invention thereto.

EXAMPLE 1

Isolation of chromosomal DNA:

Mouse hybridoma NL-1 cells ($2 \times 10^7$) obtained from Dr. R. Ueda of Laboratory of Chemotherapy, Aichi Cancer Center Research Institute, Nagoya 464, Japan were treated with protease K (Sigma Co.) in the presence of 1% SDS (sodium lauryl sulfate). Water-saturated phenol was then added to extract DNA. The aqueous layer was separated by centrifugation and dialyzed against 10 mM Tris-HCl buffer (pH 7.4) containing 0.1 mM NaCl and 0.1 mM EDTA (TNE buffer). The aqueous solution was treated with ribonuclease A (Sigma Co.), and again extracted with water-saturated phenol. The aqueous layer was dialyzed against the TNE buffer to obtain 300 micrograms of mouse chromosomal DNA.

EXAMPLE 2

Construction of a gene library:

The mouse chromosomal DNA (150 micrograms) obtained in Example 1 was completely digested with restriction endonuclease EcoRI (Takara Shuzo Co., Ltd.), and subjected to agarose gel electrophoresis. A DNA fragment (5 microgram) corresponding to 7 Kb-9 Kb was recovered from the agarose gel by electroelution.

The resulting DNA fragment (0.4 microgram) and Charon 4A vector EcoRI arms (Amersham Co.) were ligated by means of T4 DNA ligase (a product of Takara Shuzo Co., Ltc.), and packaged in vitro using a kit of Amersham Co. As a result, a mouse hybridoma NL-1 gene library ($8 \times 10^6$ PFU/microgram) was obtained.

EXAMPLE 3

Screening of immunogloblin H-chain gene:

E. coli strain LE 392 (ATCC 33572) was infected with the Charon 4A phage obtained in Example 2 containing DNA derived from mouse hybridoma NL-1 to form a plaque. Clones containing mouse antibody H-chain genes were screened by the plaque hybridization method [W. D. Benton and R. W. Davis, Science, 196, 180 (1977)] using a $^{32}$P-labelled mouse immunogloblin H-chain J gene.

This procedure led to the isolation of a gene including all V regions (a 5' flanking region, VDJ regions and an enhancer region) of mouse hybridoma NL-1 having a size of 7.9 Kb.

EXAMPLE 4

Preparation of a restriction endonuclease cleavage map:

A 7.9 Kb EcoRI fragment of the mouse hybridoma NL-1 H-chain DNA obtained in Example 3 was re-cloned into vector pBR322 and used to transform E. coli strain DH-1 (ATCC 33849). The E. coli strain was cultivated in large quantities to obtain about 1 mg of a plasmid (pBR NL-1-H) having the 7.9 Kb mouse hybridoma NL-1 H-chain DNA fragment inserted into the EcoRI site of pBR322. The pBR NL-1-H was cleaved with restriction endonucleases, EcoRI, BamHI, HindIII, EcoRV and PvuII (Takara Shuzo Co., Ltd.) and SphI (Bethesda Research Laboratory), and a restriction endonuclease cleavage map was prepared. As a typical example, cleavage with EcoRI is shown below.

One microgram of the DNA was dissolved in a buffer for digestion with restriction endonuclease [a Tris-HCl aqueous solution (pH 7.4) containing 100 mM NaCl and 10 mM MgSO$_4$] and digested with 4 units of EcoRI at 37° C. for 2 hours. The DNA was subjected to agarose gel electrophoresis and stained with 2 micrograms/ml of an aqueous solution of ethidium bromide. Its digestion pattern was analyzed by ultraviolet radiation. Thus, the cleavage sites indicated in the accompanying drawing were determined.

EXAMPLE 5

Determination of the DNA sequence:

The pBR-NL-1-H was cleaved with restriction endonucleases SphI (New England Bio Laboratories) and PvuII (Takara Shuzo Co., Ltd.) to obtain two DNA fragments given by the inserted gene between SphI and PvuII sites. The DNA fragments were cloned into M13 phage vectors mp18 and mp19 (P. L. Biochemicals Co.) cleaved with SphI and HincII (Takara Shuzo Co., Ltd.). DNA sequence determination was performed by the dideoxy chain termination method using an M13 sequencing kit (Takara Shuzo Co., Ltd.). The sequence of the SphI/PvuII fragment on the 5' side was determined both in the downstream direction from the SphI site and in the upstream direction from the PvuII site. The sequence of the SphI/PvuII fragment on the 3' side was determined in the downstream direction from the PvuII site.

We claim:

1. A DNA sequence comprising a double strand polynucleotide segment consisting of a DNA sequence (A) shown below and a DNA sequence complementary thereto:

5'-GATGTGCAGCTGGTGGAGTCTGGGGGAGGCTTA
GTGCAGCCT
GGAGGGTCCCGGAAACTCTCCTGTGCAGCCTCT
GGATTCACT
TTCAGTAGCTTTGGAATGCACTGGGTTCGTCAG
GCTCCAGAG
AAGGGGCTGGAGTGGGTCGCATATATTAGTGGT
GGCAGTTAT
ACCATCTACTATGCAGACACAGTGAAGGGCCGA
TTCACCATC
TCCAGAGACAATCCCAAGAACACCCTGTTCCTA
CAAATGACC
AGTCTAAGGTCTGAGGACACGGCCATGTATTAC
TGTGCAAGT
TCCTATGGTAACTTCTGGTACTTCGATGTCTGG
GGCGCAGGG
ACCACGGTCACCGTCTCCTCA-3' wherein A represents deoxyadenosine-5'-phosphate, C represents deoxycytidine-5'-phosphate, G represents deoxyguanosine-5'-phosphate, and T represents deoxythymidine-5'-phosphate.

2. A DNA sequence encoding a polypeptide represented by the following amino acid sequence:

Asp Val Gln Leu Val Glu Ser Gly Gly Gly Leu Val
Gln Pro Gly Gly Ser Arg Lys Leu Ser Cys Ala Ala
Ser Gly Phe Thr Phe Ser Ser Phe Gly Met His Trp
Val Arg Gln Ala Pro Glu Lys Gly Leu Glu Trp Val
Ala Tyr Ile Ser Gly Gly Ser Tyr Thr Ile Tyr Tyr
Ala Asp Thr Val Lys Gly Arg Phe Thr Ile Ser Arg
Asp Asn Pro Lys Asn Thr Leu Phe Leu Gln Met Thr
Ser Leu Arg Ser Glu Asp Thr Ala Met Tyr Tyr Cys
Ala Ser Ser Tyr Gly Asn Phe Trp Tyr Phe Asp Val
Trp Gly Ala Gly Thr Thr Val Thr Val Ser Ser wherein the various abbreviations stand for the following amino acids:
Gly: glycine
Ala: alanine
Val: valine
Leu: leucine
Ile: isoleucine
Ser: serine
Asp: aspartic acid
Lys: lysine
Arg: arginine
His: histidine
Phe: phenylalanine
Tyr: tyrosine
Thr: threonine
Cys: cysteine
Met: methionine
Glu: glutamic acid
Trp: tryptophan
Pro: proline
Asn: asparagine
Gln: glutamine.

3. The DNA sequence of claim 1 which is derived from a rearranged immunoglobulin heavy chain variable region gene taken from the cells of a mouse hybridoma, NL-1.

4. A DNA sequence of claim 1 comprising a double strand polynucleotide segment consisting of
(i) the DNA sequence (A) described in claim 1,
(ii) a DNA sequence (B) shown below

```
5'-GCATGCTATAGAGGAAGATATGCAAATAATTCTT
CTCTGAGTTCATATAAACCAGCCCTGCCCCGAGTCT
GTAGCTCTGACAGAGGAGCCAAGCCCTGGATTCCC
AGGTCCTCACATTCAGTGATCAGCACTGAACACAGA
CCACTCACCATGGACTCCAGGCTCAATTTAGTTTTCC
TTGTCCTTATTTTAAAAGGTAAATTTGTAGAGATGAG
TTTCTGCCTGTTGTGTGCCCAAGGGAAATAGAAACA
TTGTTTGTTTCATTATTTTATTTTGTTAGTAACAGTTTT
CTGACCAGCATTCTCTGTTTGCAGGTGTCCAGTGT-3'
``` wherein A, C, G and T are as defined in claim 1, and
(iii) DNA sequences complementary to these DNA sequences (A) and (B).

* * * * *

UNITED STATES PATENT AND TRADEMARK OFFICE
CERTIFICATE OF CORRECTION

PATENT NO. : 4,786,719

DATED : November 22, 1988

INVENTOR(S) : AKIRA KUDO, YUSHI NISHIMURA, YATARO ICHIKAWA and TAKESHI WATANABE

It is certified that error appears in the above-identified patent and that said Letters Patent is hereby corrected as shown below:

Column 6, rewrite line 19 as follows:

-- TTGTCCTTATTTTAAAAGGTAATTTGTAGAGATGAG --

Signed and Sealed this

Ninth Day of January, 1990

Attest:

JEFFREY M. SAMUELS

Attesting Officer     Acting Commissioner of Patents and Trademarks